United States Patent [19]

Becker et al.

[11] Patent Number: 5,187,296

[45] Date of Patent: Feb. 16, 1993

[54] CYANOHYDRINATION PROCESS

[75] Inventors: Yigal Becker, Tel Aviv; Asher Elgavi, Petach Tikva; Youval Shvo, Arsuf, all of Israel

[73] Assignee: Bromine Compounds Limited, Beer-Sheva, Israel

[21] Appl. No.: 731,434

[22] Filed: Jul. 17, 1991

Related U.S. Application Data

[62] Division of Ser. No. 447,095, Dec. 6, 1989, Pat. No. 5,057,477.

[30] Foreign Application Priority Data

Dec. 7, 1988 [IL] Israel ........................................ 88618

[51] Int. Cl.$^5$ ............................................ C07C 253/16
[52] U.S. Cl. ..................................... 558/351; 558/410
[58] Field of Search ................................ 558/351, 410

[56] References Cited

U.S. PATENT DOCUMENTS

| | | | |
|---|---|---|---|
| 4,554,102 | 11/1985 | Dong et al. | 558/351 X |
| 4,569,793 | 2/1986 | Dong et al. | 558/351 X |
| 4,594,196 | 6/1986 | Stoutamire et al. | 558/351 |
| 4,611,076 | 9/1986 | Dong et al. | 558/351 |
| 4,611,077 | 9/1986 | Dong et al. | 558/351 |
| 4,681,947 | 7/1987 | Stoutamire et al. | 544/370 |
| 4,740,615 | 4/1988 | McManus et al. | 562/446 |
| 4,837,353 | 6/1989 | Finkelstein et al. | 558/410 X |

FOREIGN PATENT DOCUMENTS

| | | |
|---|---|---|
| 135691 | 4/1985 | European Pat. Off. . |
| 205782 | 12/1986 | European Pat. Off. . |
| 304954 | 3/1989 | European Pat. Off. . |
| 2143823 | 2/1985 | United Kingdom . |

OTHER PUBLICATIONS

Crook, et al.: ITEC Product Research & Development, vol. 14, pp. 113-118, (1975).
Sukati, Journal of Organic Chemistry, vol. 50, pp. 4388-4390, (1985).
Kirk-Othmer Encyclopedia of Chemical Technology, 3rd ed., vol. 24, pp. 310-312 (1984).
Paleos, Journal of Colloid and Interface Science, vol. 31, pp. 7-18, (1969).
Bulletin of the Chemical Society of Japan, vol. 59, No. 3, 1986, pp. 893-895, Y. Kobayashi et al, "Assymetric Addition of Hydrogen Cyanide to Substituted Benzaldehydes Catalyzed by a Synthetic Cyclic Peptide, Cyclo((S)-phenylalanyl-(S)-histidyl)".
Oku, et al; J.C.S. Chem. Comm. (1981), pp. 229-230.

*Primary Examiner*—Joseph Paul Brust
*Attorney, Agent, or Firm*—Michael N. Meller

[57] ABSTRACT

A process for the assymetric cyanohydrination of m-phenoxybenzaldehyde with HCN, using a catalytically effective amount of enantiomeric cyclo(phenylalanyl-histidine) absorbed on a solid support comprising a nonionic polymer resin is described.

8 Claims, No Drawings

CYANOHYDRINATION PROCESS

FIELD OF THE INVENTION

The present invention relates to the preparation of a supported catalyst for the asymmetric cyanohydrination of m-phenoxybenzaldehyde (m-PBA), and to a process for carrying out the asymmetric cyanohydrination.

THE PRIOR ART

The compound (s)-m-phenoxbenzaldehyde cyanohydrin (m-PBAC) is an important intermediate in the synthesis of insecticidal pyrethroids. The existing industrial methods therefor are impractical and expensive, and thus the art has struggled for a long time in the attempt to provide convenient and industrially practical syntheses for this compound. The asymmetric synthesis of these cyanohydrins by the addition of hydrogen cyanide to the corresponding benzaldehyde has been attempted by Oku et al., in the presence of a synthetic dipeptide catalyst (*J.C.S. Chem. Com.*, pp. 229–230 [1981], Oku et al., Makromol. Chem. 183, 579–586 [1982], and other publications). The preparation and use of different catalyst has been addressed in various other publications and patents, such as U.S. Pat. Nos. 4,569,793, 4,594,196, 4,681,947, and GB 2 143 823. All these methods, however, suffer from different drawbacks. First of all, the reaction as carried out according to the art is very slow, and the methods employed as inconvenient from the industrial point of view. Furthermore, the requirements for purity of the product are extremely high, and according to the known art obtaining a very pure product is difficult.

SUMMARY OF THE INVENTION

It is therefore an object of the present invention to provide a catalyst by means of which the asymmetric cyanohydrination of m-PBA can be carried out easily, cheaply, and on an industrial scale. It is another object of the invention to provide a method employing such a catalyst, by means of which a highly pure product can be obtained.

DETAILED DESCRIPTION OF THE INVENTION

The catalyst according to the invention comprises an enantiomeric. cyclo (phenylalanyl-histidine) (CPH) on a solid support, the solid support being a non-ionic polymer resin. The said resins preferably comprise styrenic-divinylbenzene copolymers.

Examples of some commonly employed styrenic-divinylbenzene copolymers useful for carrying out the invention are the XAD resins, the Diaion HP resins and Sepabeads SP207. The XAD resins, also called Amberlite Polymeric Adsorbents, are described in detail in several technical bulletins of the Rohm and Haas Company, e.g., the bulletin dated 1978, and in the related patents granted to Rohm and Haas. Amberlite Polymeric Adsorbents are hard insoluble spheres of high surface, porous polymer. They usually provide a nominal mesh size of 20–60 and are available in a variety of polarities and surface characteristics. Among their various uses, Amberlite XAD-2 and XAD-4 are used, e.g., in sensitive analytical procedures to detect, identify and measure the presence of pesticides and other organics in the environment. They are also used to detect narcotics in blood and urine. XAD-4 is also used for treating "drug overdose" victims throughout the world, by passing the blood of the person being treated through a cartridge containing the resin. The physical properties of the Amberlite Adsorbents are summarized in Table I as taken from the mentioned 1978 Rohm and Haas bulletin. Among the various XAD resins, XAD-4 is considered the most convenient, since it provides conversions up to 96% with enantiomeric excesses of up to 98.5%. Other XAD resins, such as XAD-7, XAD-16, XAD-1180, are suitable for carrying out the invention, although, as said, XAD-4 is preferred.

TABLE I

Typical properties of Amberlite polymeric adsorbents

| | Chemical Nature | Porosity Vol. % | True Wet Density gr/cc | Surface Area sqm/gr Nonpolar | Average Pore Dia. Angstrom | Skeletal Density gr/cc | Nominal Mesh Sizes |
|---|---|---|---|---|---|---|---|
| XAD-1 | Polystyrene | 37 | 1.02 | 100 | 100 | 1.07 | 20 to 60 |
| XAD-2 | Polystyrene | 42 | 1.02 | 300 | 90 | 1.07 | 20 to 60 |
| XAD-4 | Polystyrene | 45 | 1.02 | 725 | 40 | 1.08 | 20 to 60 |

Sepabeads SP207, as well as the Diaion HP resins, such as HP-20, HP-30 and HP-40 polymers (Mitsubishi Chemical Industries Ltd.), are useful in similar applications, e.g., for recovering amino acids from mixtures thereof (U.S. Pat. No. 4,740,615).

Surprisingly, it has been found that preparing a CPH on solid supports which are conventionally employed for catalyst preparation, such as activated carbon, alumina and so on, results in a catalyst which is not active or very slightly active.

Another object of the invention is to carry out the asymmetric cyanohydrination of m-PBA, catalysed by (L,L) or (D,D)-CPH. Some important factors which should be taken into account, when carrying out this reaction, are: (a) the concentration of the catalyst, (b) the concentration of m-PBA, and (c) the temperature at which the reaction takes place. Other factors of importance are the order of addition of reactants, the excess of HCN, the solvent of the reaction, and the mode of operation (batch operation or loop operation, viz., recirculation over a stationary catalyst). The typical chemical and optical EE yields of m-PBAC obtained according to the process of the invention, are in the range of at least 82 to at least 98%, and the dominating configuration obtained is opposite to that of the enantiomeric CPH used in the reaction. The molar excess of HCN should preferably be in the range of 1.7 to 2.57, but lower excesses are also possible.

The quantity of the enantiomeric catalyst, expressed in mole % CPH relative to m-PBA used in the reaction should preferably be in the range of 0.75 to 2. Concentrations below 0.75 do not afford high enough conversions, even under prolonged reaction periods such as 8 hours. Under these conditions the conversion usually will not exceed 90%, while higher values of CPH result in practically complete conversion. High enantiomeric excesses, however, are obtained both at low and high catalyst concentration. Higher catalyst concentrations, on the other hand, may adversely affect the enantiomeric excess, due to competing racemization.

The concentration of m-PBA in the reaction mixture affects the rate of reaction, as well as the conversion and the enantiomeric excess. Concentrations of m-PBA below 15 volume % result in conversions lower than 90% and EE higher than 90%, between 15 vol. % and 23 vol. % conversions of 95-200% are obtained, with EE greater than about 95-98%, and between 34-84 vol. % the conversion is about 100%, and the EE drops to 85-26%.

High conversions are obtained in the reaction according to the invention at virtually all practical temperatures. The reaction proceeds to high conversions at $-5°$ C. as well as $+25°$ C. However, the lower the temperature, the higher the enantiomeric excess. At room temperature, the obtainable enantiomeric excess is in the order of 74-75%, at 10° C. EE values are around 90%, and at 0° C. and below, 95% or higher values are obtained. This, as will be apparent to a person skilled in the art, is due also to the undesired reaction of the product in the presence of the catalyst, which is promoted by higher temperatures.

The preferred solvent for the reaction is toluene. However, other solvents can be employed as well, as is apparent to a person skilled in the art, such as benzene, ethers, e.g., diethyl or diisopropyl ether, and their mixtures with toluene. Hydrocarbon solvents such as petrol ether give very high conversions, but very low EE. Halogenated hydrocarbons, such as $CCl_4$, can also be employed, but they mostly result in unsatisfactory conversions and EE.

The catalysts can be prepared, in a way known to the man of the art, by adsorbing the cyclic dipeptide (CPH), from an appropriate solution, on the XAD. A preferred way of doing so is to pass the solution of CPH through a column containing the solid support. Very low concentration solutions (e.g., 0.1% CPH in water) can be employed. After the required amount of CPH has been adsorbed on the XAD, the column can be washed with a non-reactive solution, in order to remove non-adsorbed material, and then dried. The temperature at which the column is dried should not exceed 100° C. and the catalyst obtained is ready and immobilized in the column. For further details on these standard procedures, reference is made to the Rohm and Haas Summary Bulletin referred to above.

It should be noted that in the catalytic systems obtained, the CPH supported on solid support, consists of a molecular layer of cyclo(phenylalanylhistidine) on the solid support. It is believed that this adsorption provides an activated monolayer of single molecules, and that this is responsible for the high efficiency and selectivity of the solid supported catalyst. Furthermore, the catalyst so prepared has a great advantage over the prior art catalysts. The catalysts known in the prior art provide an inconsistent performance, possibly due to a physical change during the reaction. Thus, it is difficult to control a reaction in which the catalyst activity substantially changes with time. In contrast, the solid supported catalyst of the invention is 100% active from the very beginning, does not undergo physical changes to any appreciable extent, and is therefore substantially constant in performance.

It has further surprisingly been found that the overall reaction times obtained with the catalyst of the invention are substantially shorter than known in the art, which permits to carry out continuous or semi-continuous reactions, in which the catalyst is immobilized rather than suspended. As will be appreciated from the following examples, operating according to the invention, with recirculation, results in 95-96.5% conversions after 2.5 hours at 0° C., with an EE of 97.6-86.7%. These indicative results can be compared, e.g., with U.S. Pat. No. 4,611,076, Table 2, which reports results obtained at 25° C. In Experiment 1, after 2 hours, a 95.9% conversion is obtained with an EE of 80%. This, in view of the difference in reaction temperatures, represents a considerable difference in reaction rates.

The reaction can be carried out in a batch mode, by dispersing the solid catalyst in the reaction mixture, in which case at the completion of the reaction the catalyst can be filtered out, recovered and reused. On the other hand, the nature of the catalyst of the invention is such as to permit continuous reactions with or without recirculation to be carried out. This practically means that the reaction can be effected by passing the reaction mixture through the column containing the catalyst, either by recirculating the mixture several passes through the same column (semi-batch operation), or by providing a cascade of a number of such columns (continuous operation).

The above and other characteristics and advantages of the invention will be better understood through the following illustrative and non-limitative examples thereof.

EXAMPLE 1

Preparation of CPH on Solid Support Catalysts-General Procedure

The following catalysts, composed of enantiomeric cyclo (phyenylalanylhistidine), (CPH), on solid supports, were prepared by passing a solution of cyclic dipeptide (CPH) in water (0.1%) through a column containing the solid support. After the prescribed amount of CPH was charged on the support, the column was washed with water to remove any traces of non-absorbed CPH, and dried in vacuum oven (80° C.).

The efficiencies of the catalysts, thus obtained, were tested by a batchwise cyanohydrination of m-phenoxybenzaldehyde with hydrocyanic acid in toluene. The specific catalysts, conversions, and enantiomeric excess are listed in the Table II below.

TABLE II

Asymmetric addition of hydrogen cyanide to m-Phenoxybenzoldehyde catalysed by L,L or D,D CPH on solid supports.

| Solid Support | L,L-/DD-CPH/Solid Support (%) | | Conversion (%) | Enantiomeric Excess (%) |
| --- | --- | --- | --- | --- |
| XAD-7 | (L,L) | 2.1 | 76 | 18.8 |
| XAD-4 | (D,D) | 5.85 | 96 | 98.5 |
| Kieselgel 60 | | 0.0 | — | — |
| Chromosorb | | 0.0 | — | — |
| Charcoal (Chromatog.) | (L,L) | 5.0 | 48 | 33.2 |
| Charcoal (Powder) | (L,L) | 6.5 | 95.2 | 1.0 |
| XE305 | | 0.0 | — | — |
| XAD-16 | (D,D) | 6.46 | 81.6 | 87.5 |
| XAD-1180 | (D,D) | 5.0 | 70.5 | 87.8 |
| Charcoal (3mm) | (D,D) | 4.93 | — | — |

EXAMPLE 2

Preparation of (s)-m-Phenoxybenzaldehyde cyanohydrin m-Phenoxybenzaldehyde (105 g, 530 mmole) was added to the catalyst (D,D-CPH/XAD-4; 45.3 g contains 2.65 g D,D-CPH) and left for 5 min. Consequently toluene (520 ml) and HCN (1 ml) were added and left overnight at +5° C. under nitrogen. Hydrogen cyanide (34 ml) was added and the mixture was mechanically stirred for 4 hrs. in an ice bath. The catalyst was filtered off and washed with toluene (100 ml). The combined filtrate and washings were twice extracted with HCl (1M, 50 ml) and with water to neutrality. Dodecylbenzene sulfonic acid (240 mg) was added as stabilizer. Similarly, $Et_3NH+HSO_4-$ was also employed in some cases for the same purpose.

Evaporation of the solution under water pump and then under high vacuum gave the product, 115 gr.

| Analysis: | m-PBAC | 89.77% |
|---|---|---|
| | free CN | 92 ppm |
| | % $H_2O$ (Karl Fisher) | 461 ppm |
| | $[\alpha]_D =$ | −24.43° (466 mg, 10 ml $CHCl_3$) |
| | Enantiomeric excess | 98.5% |

D,D-CPH: cyclo-D-phenylalanyl-D-histidine
m-PBAC: m-Phenoxybenzaldehyde cyanohydrin

EXAMPLE 3

Example 2 was repeated, but using different reaction conditions, and either (D,D) or (L,L)-CPH. The results of 25 runs are detailed in Table III, together with the reaction conditions for each run. The m-PBA concentration in the table is defined as:

$$m\text{-}PBA\ concentration(\%) = \frac{m\text{-}PBA\ (volume)}{Total\ volume\ of\ solution} \times 100$$

EXAMPLE 4

Example 2 was repeated, with the exception that the solvent was replaced with different solvents. Six experimental runs were carried out, each with a different solvent.

All experiments were carried out at 20° C. and stopped after 4 hours. The results are detailed in Table IV.

TABLE III

Asymmetric Cyanohydrination of m-PBA
Characteristic Conditions and Results

| Reaction No. | $CPH^a$/ m-PBA mole % | m-PBA conc. | Reaction Temp. °C. | Time hr | Conversion % | ee % |
|---|---|---|---|---|---|---|
| 1(L,L) | 1.89 | 8.0 | r.t. | 3.5 | 78 | 44 |
| 2(L,L) | 1.50 | 8.0 | 0 | 4.3 | 91.7 | 92.6 |
| 3(L,L) | 0.50 | 14.8 | r.t. | 4.3 | 61.2 | 74.7 |
| 4(L,L) | 1.55 | 8.0 | 0 | 4.5 | 89.6 | 93 |
| 5(L,L) | 1.49 | 8.0 | 0 | 4.5 | 88.2 | 92.7 |
| 6(D,D) | 1.52 | 14.9 | 0 | 4.0 | 94.7 | 89.2 |
| 7(D,D) | 0.75 | 14.9 | 0 | 13.0 | 82 | 86 |
| 8(D,D) | 0.76 | 14.9 | 0 | 7.0 | 89.5 | 82.4 |
| 9(D,D) | 1.52 | 20.8 | 0 | 4.0 | 97.4 | 89.2 |
| 10(D,D) | 1.50 | 21.2 | −2 | 4.0 | 93.7 | 85.9 |
| 11(D,D) | 1.28 | 22.5 | −5 | 5.0 | 93.7 | 89.9 |
| 12(D,D) | 1.53 | 22.7 | −3 | 4.0 | 98.0 | 98.2 |
| 13(L,L) | 1.94 | 15.0 | 0 | 4.0 | 98.0 | 93.4 |
| 14(L,L) | 1.0 | 14.8 | 0 | 4.0 | 88.3 | 93.6 |
| 15(L,L) | 1.89 | 15.5 | +10 | 4.0 | 98.4 | 92.9 |
| 16(L,L) | 1.85 | 15.8 | 0 | 4.0 | 98.6 | 94.7 |
| 17(D,D) | 2.0 | 14.8 | 0 | 4.5 | 99.4 | 86 |
| 18(L,L) | 2.0 | 14.8 | 0 | 4.5 | 100 | 91 |
| 19(L,L) | 2.0 | 34.0 | 0 | 4.5 | 100 | 85 |
| 20(L,L) | 1.0 | 34.2 | +10 | 7.0 | 86.7 | 63 |
| 21(L,L) | 2.0 | 84.0 | +10 | 4.0 | 100 | 26.6 |
| 22(L,L) | 1.0 | 84.0 | +10 | 4.0 | 100 | 20.2 |
| $23^b$(D,D) | 1.0 | 15.0 | 0 | 8.0 | 81.6 | 87.5 |

TABLE III-continued

Asymmetric Cyanohydrination of m-PBA
Characteristic Conditions and Results

| Reaction No. | $CPH^a$/ m-PBA mole % | m-PBA conc. | Reaction Temp. °C. | Time hr | Conversion % | ee % |
|---|---|---|---|---|---|---|
| $24^c$(D,D) | 1.0 | 15.0 | 0 | 8.0 | 70.5 | 87.8 |
| 25(D,D) | 1.73 | 15.0 | 0 | 4.0 | 95.8 | 92.3 |

$^a$CPH/XAD-4; $^b$CPH/XAD-16; $^c$CPH/XAD-1180
(D,D) = D,D-CPH; (L,L) = L,L-CPH

TABLE IV

Asymmetric cyanohydrination in different solvents

| Solvent | Conversion % | ee % |
|---|---|---|
| $t\text{-}BuOCH_3$ | 85.0 | 40.6 |
| $i\text{-}Pr_2O$ | 72.3 | 78.2 |
| 25% $i\text{-}Pr_2O$/Tol. | 85.9 | 72.6 |
| $Et_2O$ | 88.4 | 61.4 |
| $CCl_4$ | 70 | 51.4 |
| Petrol ether 60–80% | 98.4 | 9.1 |

EXAMPLE 5

Preparation of Optically Active
m-PBAC-Cyanohydrination of m-PBA by recirculation The catalyst (6.8 g, 5.85% D,D-CPH/XAD-4) packed in a short column equipped with a cooling jacket was charged with m-PBA (3.47 g) and toluene (17.5 ml), and left overnight at +5° C. The column was connected at the bottom to a three neck flash containing the rest of the reactant m-PBA (10.4 g) in toluene (49 ml), and the solution was circulated through the top of the column by a metering pump. The system was cooled in ice/water bath and then hydrocyanic acid (4.6 ml) was added to the flask. The reaction mixture was recycled at a rate of 60 ml/min. through the column. After 2.5 hrs, the circulation was stopped and the content of the column was washed with toluene (60 ml). The reaction mixture was extracted with phosphoric acid (0.1M, 2×50 ml) and with water (3×50 ml) to neutrality, to remove all the cyclic peptide D,D-CPH without any damage. The extractions and washings were combined and brought to 380 ml and pH 8.15 with ammonium hydroxide, $\alpha_D=+0.103°$ (estimated 301 mg D,D-CPH-Solution A). The organic phase, after evaporation of the toluene has a conversion of 96.5% and an assay of 89.1% m-PBAC, $\alpha_D=0.722°$ (0.396 g, 10 ml $CHCl_3$) corresponding to an enantiomeric excess of 87.6%. The catalyst in the column was washed with methanol (200 ml) to remove the rest of the adsorbed D,D-CPH. Evaporation of the methanol extract to dryness and washing the residue with toluene (20 ml) left clean D,D-CPH which was redissolved in water (250 ml) containing phosphoric acid (10 ml 0.1M). This filtered solution has $\alpha_D=+0.045°$ (estimated D,D-CPH-90 mg, solution B). The pH was adjusted to 8.15 with ammonium hydroxide.

The resin in the column was prepared for recharge with the extracted D,D-CPH for the next operation by washing with methanol/water and water. D,D-CPH solutions A and B above, were passed through the column. All the D,D-CPH was adsorbed. Passing additional water (100 ml) through the column proves that no leak of the D,D-CPH took place.

The catalyst thus recharged was dried in a vacuum oven (80° C.) and was ready for the next cyanohydrination reaction. The catalyst was so recycled five times, without any appreciable loss of the cyclic dipeptide. Conversations and assays were determined by NMR method. The results are listed in Table V below. The EE values of Table V were calculated on the basis of results obtained by NMR techniques. Results of potentiometric assay normally indicate higher EE values.

TABLE V

Asymmetric addition of HCN to m-PBA catalysed by D,D-CPH/XAD-4 in a circulation process

| Cycle No. | Conversion % | ee % |
|---|---|---|
| 1 | 96.5 | 87.6 |
| 2 | 95.7 | 93.3 |
| 3 | 93.2 | 86.7 |
| 4 | 95.3 | 93.5 |
| 5 | 95.0 | 97.6 |

The above description and examples have been given for purpose of illustration and are not intended to be limitative. The skilled chemist will be able to effect many changes in the materials and methods employed herein, which are within the skill of the routineer, and which do not exceed the scope of the invention.

We claim:

1. A process for the preparation of (s)-m-phenoxybenzaldehyde cyanohydrin, comprising contacting m-phenoxybenzaldehyde with HCN in a suitable cyanohydrination solvent with a catalytically effective amount of a catalyst which is enantiomeric cyclo-(phenylalanine-histidine), absorbed on a solid support of a non-ionic polymer resin.

2. A process according to claim 1, wherein the solvent is selected from the group consisting of toluene, benzene, ethers and mixtures thereof.

3. A process according to claim 1, wherein the catalyst is immobilized in a column and the reaction mixture is passed therethrough.

4. A process according to claim 3, wherein the reaction is effected in semi-batch mode by recirculating the reaction mixture from and to a reservoir, through the immobilized catalyst.

5. A process according to claim 1, wherein the non-ionic polymer resin comprises a styrene-divinylbenzene copolymer.

6. A process according to claim 5, wherein the styrene-divinylbenzene copolymer of the catalyst is selected from the group consisting of the XAD resins, the Diaion HP resins and Sepabead SP207.

7. A process according to claim 6, wherein the XAD resin is XAD-4.

8. A process for the preparation of (s)-m-phenoxybenzaldehyde cyanohydrin, comprising contacting m-phenoxybenzaldehyde with HCN is a suitable cyanohydrination solvent with a catalytically effective amount of a catalyst which is cyclo-(D-phenylalanyl-D-histidine), on a non-ionic polymer resin solid support.

* * * * *